(12) United States Patent
Archambault

(10) Patent No.: US 8,281,494 B2
(45) Date of Patent: Oct. 9, 2012

(54) SURGICAL BLADE

(76) Inventor: Katya Archambault, Victoriaville (CA)

( * ) Notice: Subject to any disclaimer, the term of this patent is extended or adjusted under 35 U.S.C. 154(b) by 316 days.

(21) Appl. No.: 12/542,980

(22) Filed: Aug. 18, 2009

(65) Prior Publication Data

US 2010/0049229 A1 Feb. 25, 2010

Related U.S. Application Data

(60) Provisional application No. 61/090,298, filed on Aug. 20, 2008.

(51) Int. Cl.
*B26B 21/54* (2006.01)
*B26B 3/00* (2006.01)
*A61B 17/32* (2006.01)
(52) U.S. Cl. .............. 30/346.52; 30/357; 606/167
(58) Field of Classification Search .............. 606/167, 606/172, 184; 83/522.15–522.25; 7/118, 7/119, 158, 163; 30/346.52, 357
See application file for complete search history.

(56) References Cited

U.S. PATENT DOCUMENTS

| 2,877,553 | A | * | 3/1959 | Matwijcow | 30/339 |
| 5,217,476 | A | * | 6/1993 | Wishinsky | 606/167 |
| 6,044,566 | A | * | 4/2000 | Ries et al. | 30/345 |
| 6,220,133 | B1 | * | 4/2001 | Gosselin | 83/13 |
| 6,656,186 | B2 | * | 12/2003 | Meckel | 606/82 |
| 2006/0070186 | A1 | * | 4/2006 | Karlstedt | 7/105 |
| 2007/0156164 | A1 | * | 7/2007 | Cole et al. | 606/187 |

* cited by examiner

*Primary Examiner* — Ryan Severson
*Assistant Examiner* — Ashley Cronin
(74) *Attorney, Agent, or Firm* — Brouillette & Partners; François Cartier; Robert Brouillette

(57) ABSTRACT

A surgical blade adapted to be typically used in medical procedures is disclosed. The blade is provided with markings located near the cutting edge. The markings are configured to be indicative of the depth of the blade and/or of the cutting edge during the incision of an organic tissue. The markings are configured to substantially follow the shape of the cutting edge such as to indicate the depth of the blade substantially independently of the orientation thereof.

34 Claims, 6 Drawing Sheets

SURGICAL BLADE

CROSS-REFERENCE TO RELATED APPLICATIONS

The present patent application claims the benefits of priority of U.S. Provisional Patent Application No. 61/090,298, entitled "Surgical Blade" and filed at the United States Patent and Trademark Office on Aug. 20, 2008, the content of which is incorporated herein by reference.

FIELD OF THE INVENTION

The present invention generally relates to the field of medical instruments and more particularly to the field of surgical instruments using blades.

BACKGROUND OF THE INVENTION

Scalpels and other cutting tools have long been used in surgeries and other medical procedures involving the cutting of organic tissues. To accommodate the different types of surgeries now performed, different types of surgical blades have been devised. For instance, some blades have been particularly designed for ocular surgery whereas other blades have been designed for dental surgery.

Still, despite the evolution in the design of surgical blades, certain characteristics remain deficient. For instance, depth-indicative markings provided on certain surgical blades are still rudimentary and particularly dependent upon the orientation of the blade during use. Consequently, there is still room for further improvements.

SUMMARY OF THE INVENTION

The principles of the present invention are generally embodied in a surgical blade provided with depth marks which are substantially parallel to the cutting edge(s) of the blade.

By having such depth marks on the blade, the depth marks always provide indication of the depth of the incision substantially independently from the orientation of cutting edge of the blade with respect to the tissue.

The features of the present invention which are believed to be novel are set forth with particularity in the appended claims.

BRIEF DESCRIPTION OF THE DRAWINGS

The above and other objects, features and advantages of the invention will become more readily apparent from the following description, reference being made to the accompanying drawings in which.

DETAILED DESCRIPTION OF THE PREFERRED EMBODIMENT

A novel surgical blade will be described hereinafter. Although the invention is described in terms of specific illustrative embodiments, it is to be understood that the embodiments described herein are by way of example only and that the scope of the invention is not intended to be limited thereby.

The present invention is preferably, though not necessarily, embodied in a surgical blade which is provided with marks which are indicative of depth and which are substantially parallel to the cutting edge(s) of the blade. Such a blade always provides indication of the depth of the incision performed substantially independently from the orientation of the cutting edge of the blade with respect to the tissue.

Figure 1A:
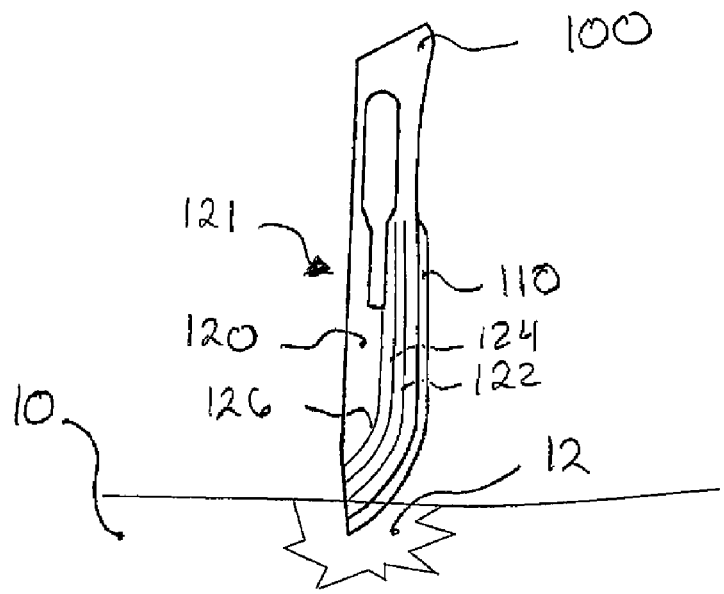
FIGS. 1A and 1B are side views showing an exemplary blade embodying the principles of the invention in two different orientations.
Figure 1B:
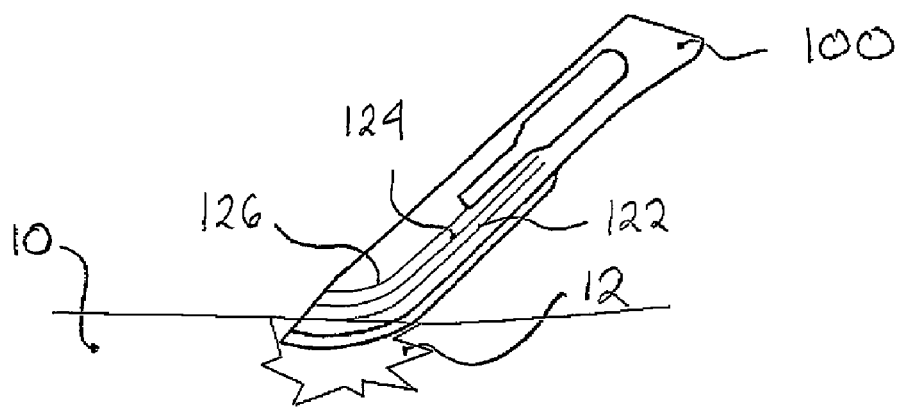

Hence, referring first to FIGS. 1A and 1B, a blade 100 embodying the principles of the invention is depicted in two different orientations. As depicted in the figures, the blade 100 is substantially flat and planar and comprises a first side or surface 120 and a second side or surface 121 (not shown) defining a cutting edge 110 having a particular shape or configuration. Also, in accordance with the invention, the blade 100 comprises, on at least one of the first and second surfaces, markings 122, 124 and 126 which are indicative of the depth of the blade 100 when an incision is performed and which are substantially parallel to the cutting edge 110.

In FIG. 1A, the blade 100 is substantially perpendicular to the tissue 10 (e.g. skin, gum, etc.) and to the incision 12. In this exemplary setting, the depth of the blade 100 is indicated by marking 122.

In FIG. 1B, the orientation of the blade 100 has changed from about 90° to about 45°. Still, due to the fact that the markings 122, 124 and 126 follow the shape of the cutting edge 110, the depth of the blade 100 is still indicated by marking 122. Hence, even if the orientation of the blade 100 has changed, the surgeon (or any other user) can still refer to the marking 122 as an indication of the depth of the blade 100, the depth remaining substantially constant along a marking.

As the skilled addressee will understand and as it will be shown, the principles of the present invention can be embodied on blades having different shapes and/or different configurations. In addition, the depth markings, which can be provided on one or both surfaces of the blade, can be provided using various visual indicators such as, but not limited to, lines (e.g. etched, raised, continuous, dashed, dotted, etc.), textured areas (e.g. polished, patterned, brushed, sand blasted, embossed, etc.) and colored areas (e.g. alternating, powder coating, etc.).

Figure 2A:
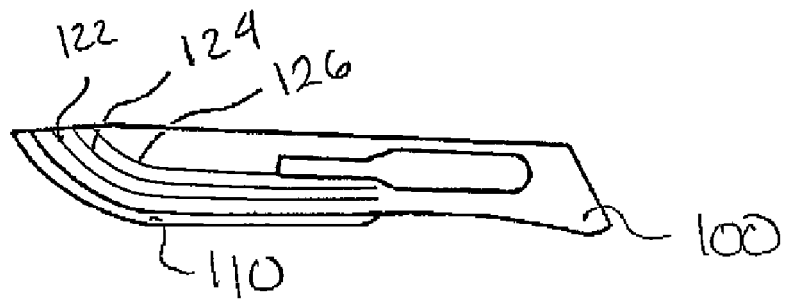
FIGS. 2A to 2C are side views of three different configurations of a first exemplary blade embodying the principles of the invention.
Figure 2B:
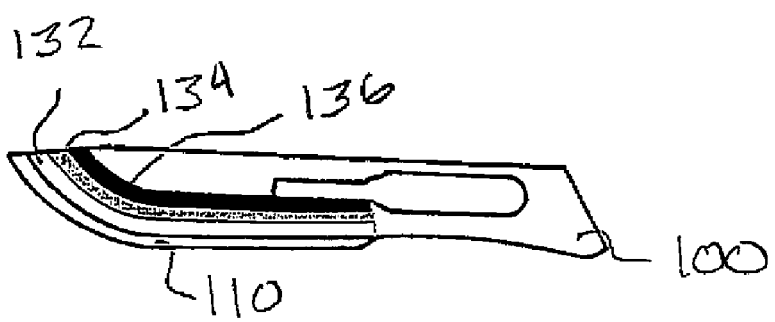
Figure 2C:
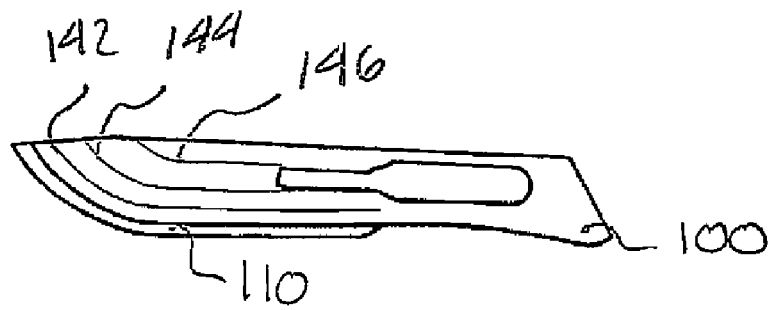

For instance, in FIGS. 2A to 2C, three configurations of the blade 100, which was previously introduced above, are shown. In FIG. 2A, the blade 100 has a cutting edge 110 having a curved shape. The blade 100 also comprises depth markings 122, 124 and 126 which, in accordance with the invention, are substantially parallel to the cutting edge 110. In this configuration, the markings 122, 124 and 126 are provided as continuous lines which are substantially equidistant from each other. In a preferred though not limitative embodiment, the markings 122, 124 and 126 are etched into the blade material. Preferably, markings 122, 124 and 126 are provided on both surfaces of the blade 100.

In FIG. 2B, the markings 132, 134 and 136 are provided as regions or areas having different texture or color (shown by the white, grey and black areas).

In FIG. 2C, the markings 142, 144 and 146 are provided as continuous lines which are not equidistant from each other.

Figure 3A:
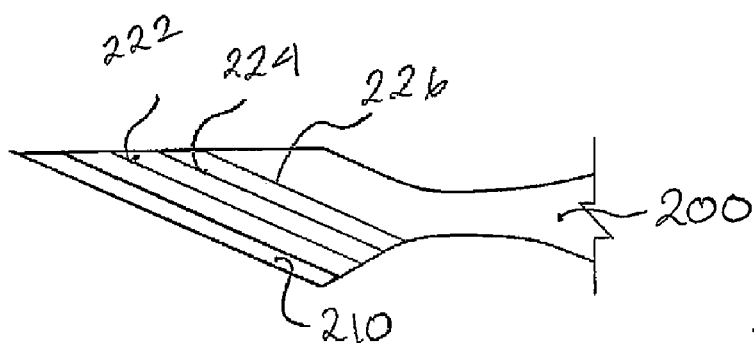
FIGS. 3A to 3C are side views of three different configurations of a second exemplary blade embodying the principles of the invention.
Figure 3B:
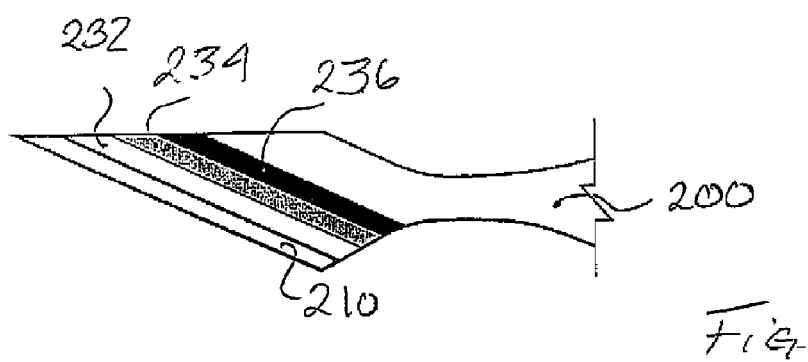
Figure 3C:
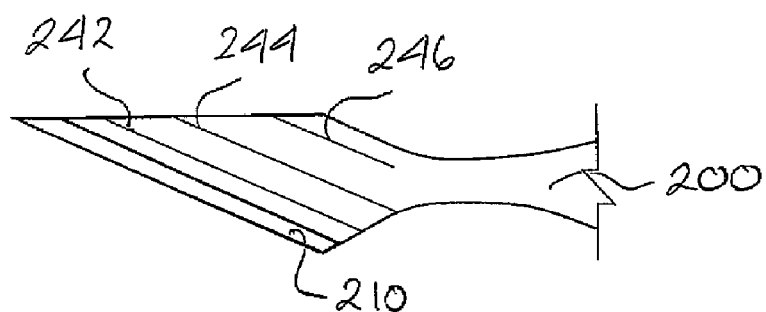

Referring now to FIGS. 3A to 3C, three configurations of a second exemplary blade 200 are shown. In FIGS. 3A to 3C, the blade 200 has a straight cutting edge 210. Still, in each of the three configurations, the markings are parallel to the cutting edge 210. In FIG. 3A, the markings 222, 224 and 226 are equidistant continuous lines, in FIG. 3B, the markings 232, 234 and 236 are areas of different textures or colors, and in FIG. 3C, the markings 242, 244 and 246 are non-equidistant continuous lines.

Figure 4A:
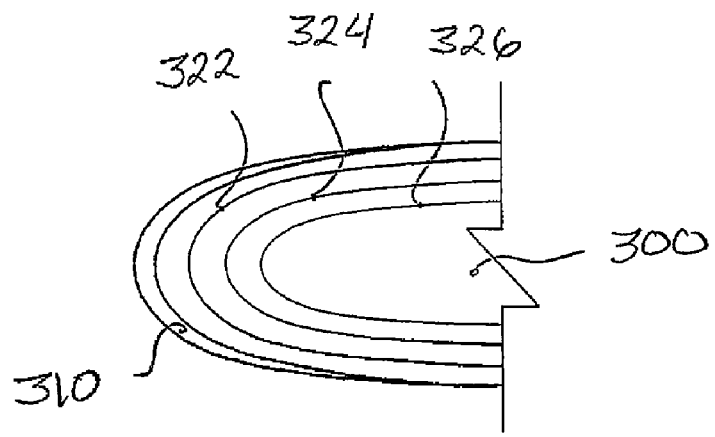
FIGS. 4A to 4C are side views of three different configurations of a third exemplary blade embodying the principles of the invention.
Figure 4B:
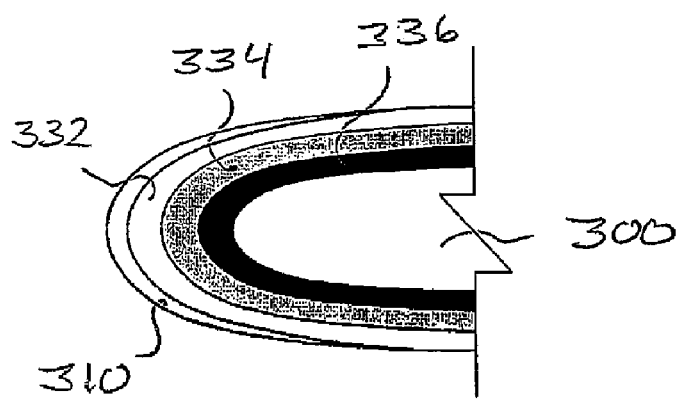
Figure 4C:
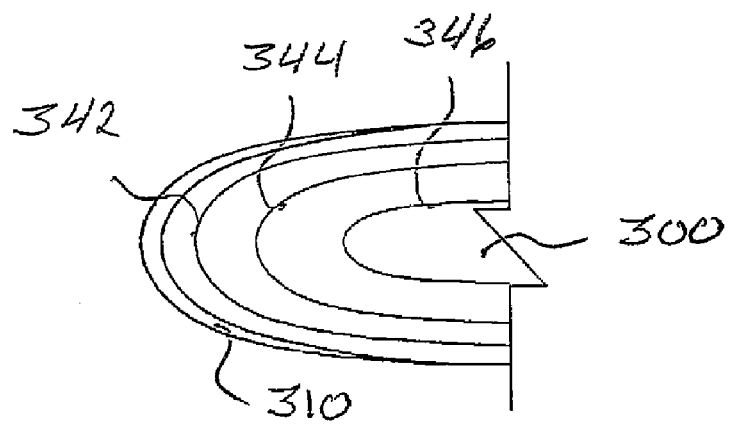

Referring to FIGS. 4A to 4C, three configurations of a third exemplary blade 300 are shown. In FIGS. 4A to 4C, the blade 300 has a substantially U-shaped cutting edge 310. Still, in each of the three configurations, the markings are parallel to the cutting edge 310. In FIG. 4A, the markings 322, 324 and 326 are equidistant continuous lines, in FIG. 4B, the markings 332, 334 and 336 are areas of different textures or colors, and in FIG. 4C, the markings 342, 344 and 346 are non-equidistant continuous lines.

Figure 5A:
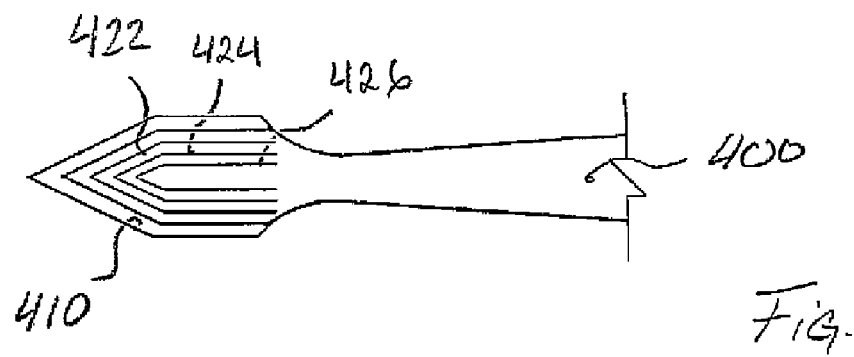
FIGS. 5A to 5C are side views of three different configurations of a fourth exemplary blade embodying the principles of the invention.
Figure 5B:
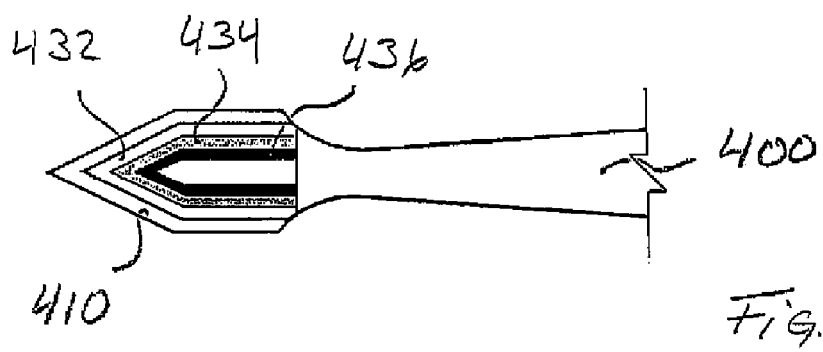
Figure 5C:
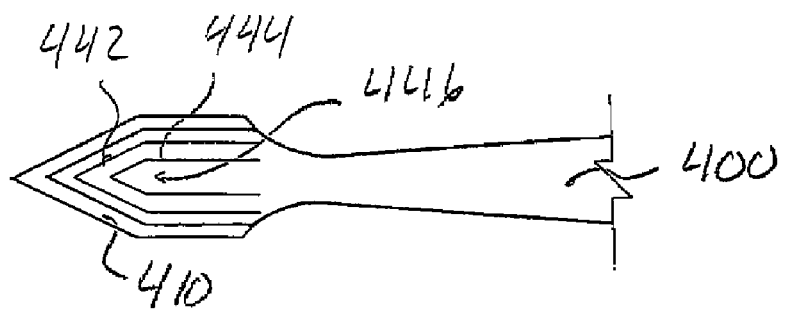

Referring finally to FIGS. 5A to 5C, three configurations of a fourth exemplary blade 400 are shown. In FIGS. 5A to 5C, the blade 400 has an approximately V-shaped cutting edge 410. Still, in each of the three configurations, the markings are parallel to the cutting edge 410. In FIG. 5A, the markings 422, 424 and 426 are equidistant continuous lines, in FIG. 5B, the markings 432, 434 and 436 are areas of different textures or colors, and in FIG. 5C, the markings 442, 444 and 446 are non-equidistant continuous lines.

Understandably, though only three markings are present in the blades shown in FIGS. 2A to 5C, it is to be understood that the actual number of markings can vary according to several factors such as, but not limited to, the size and purpose of the blade. Moreover, specialized blades used, for instance, in dental surgeries, may be provided with a specific configuration of markings. Hence, the present invention is therefore not limited to the blades shown in the figures.

The person skilled in the art will appreciate that blades embodying the principles of the invention are typically adapted to be mounted to handling tools such as, but not limited to, scalpel handles.

Figure 6:
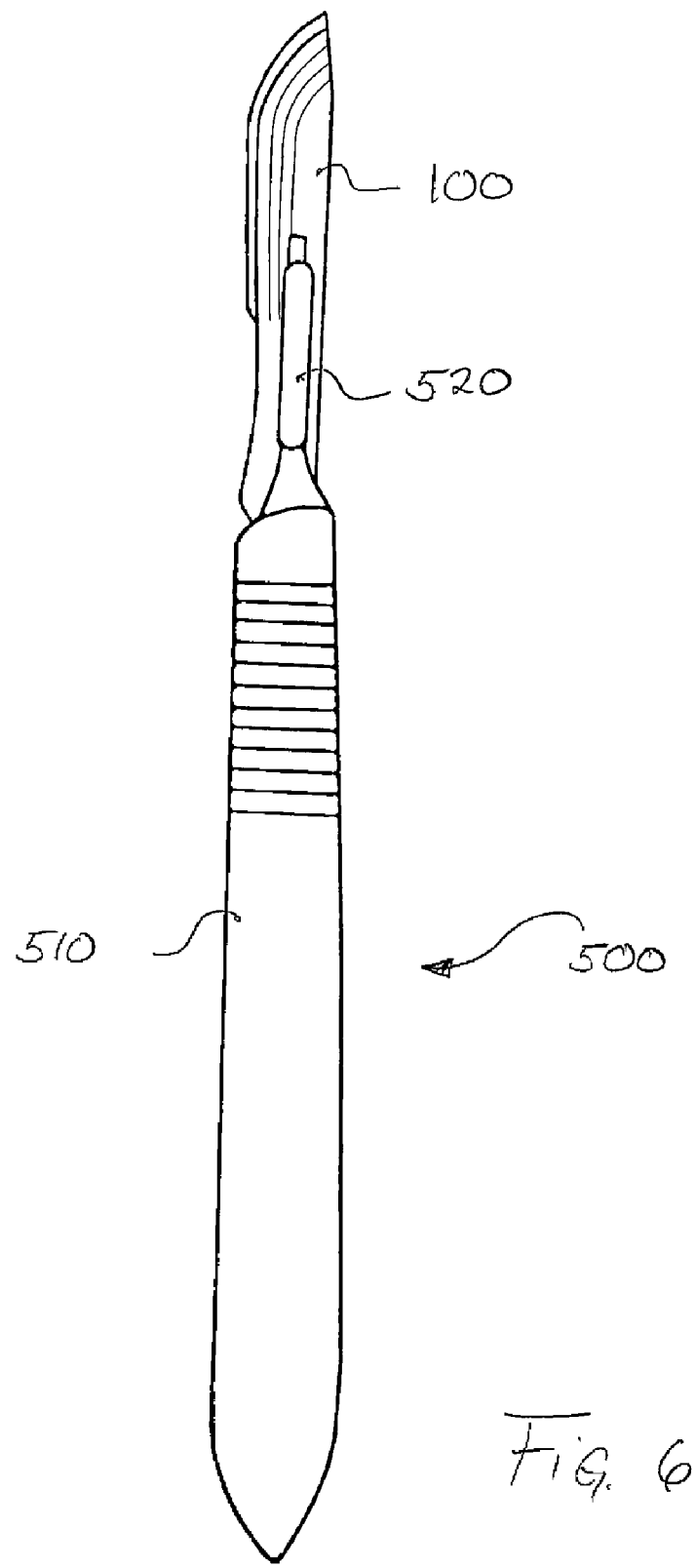
FIG. 6 is a side view of a handling tool having mounted thereto an exemplary blade embodying the principles of the invention.

In that sense, FIG. 6 depicts an exemplary scalpel 500 having mounted thereto a blade 100 as shown in FIG. 2*a*. Understandably, the scalpel 500 is of conventional configuration and therefore comprises a handle portion 510 and a mounting portion 520 extending at one extremity of the handle portion 510. The handle portion 510 is typically configured to be manipulated by a human hand whereas the mounting portion 520 is configured to releasably receive and engage the blade 100. Understandably, the blade 100 could be unitary with the handling tool; the present invention is not so limited.

From the foregoing, the skilled addressee will understand that to use the surgical blade of the present invention, the user generally has to first mount the blade to a handling tool such as a scalpel 500.

Once mounted, the user can use the blade to perform an incision or a cut. If the depth of the incision is important, the user can insert the blade into the tissue until the outer surface of the tissue reaches one of the markings as best depicted in FIG. 1A. Then, the user can increase the size of the incision by displacing the blade using the handling tool. To have an incision having a constant depth, the user only needs to keep the outer surface of the tissue aligned with the selected marking. Advantageously, as the markings are parallel to the cutting edge of the blade, the depth of the incision will not change even if the orientation of the blade changes as shown in FIG. 1B.

As shown and explained above, by having a surgical blade having markings indicative of depth which are substantially parallel to the cutting edge of the blade, the depth indicating markings of the blade can be used independently of the orientation of the cutting edge. The person skilled in the art will thus understand that such a blade provides a valuable tool for performing cleaner and more precise incision(s) during medical procedures wherein the depth of the incision(s) is important if not critical.

While illustrative and presently preferred embodiments of the invention have been described in detail hereinabove, it is to be understood that the inventive concepts may be otherwise variously embodied and employed and that the appended claims are intended to be construed to include such variations except insofar as limited by the prior art.

The invention claimed is:

1. A surgical blade, said blade being substantially planar and comprising two sides and a cutting edge, at least one of said sides comprising markings substantially following said cutting edge, said markings being configured to provide a substantially constant indication of a selected depth of said cutting edge with respect to a tissue when an orientation of said blade with respect to said tissue is changed.

2. A blade as claimed in claim 1, wherein said markings are parallel lines.

3. A blade as claimed in claim 1, wherein said markings are areas provided on the blade, each of said areas being visually different from areas adjacent thereto.

4. A blade as claimed in claim 3, wherein said areas are textured.

5. A blade as claimed in claim 1, wherein distances between adjacent markings are substantially equal.

6. A blade as claimed in claim 1, wherein said cutting edge is substantially curved.

7. A surgical blade, said blade being substantially planar and comprising a first surface, a second surface, and a substantially curved cutting edge, wherein at least one of said first and second surfaces comprises markings substantially parallel to said cutting edge, said markings being configured to provide a substantially constant indication of a depth of said cutting edge with respect to a tissue when an orientation of said blade with respect to said tissue is changed.

8. A blade as claimed in claim 7, wherein said markings are lines.

9. A blade as claimed in claim 8, wherein said lines are formed on said blade.

10. A blade as claimed in claim 8, wherein said lines are equidistant.

11. A blade as claimed in claim 7, wherein said markings are visually different areas.

12. A blade as claimed in claim 11, wherein said areas are textured.

13. A blade as claimed in claim 7, wherein both said first surface and said second surface comprise markings substantially parallel to said cutting edge.

14. A surgical blade in combination with a handling tool, said handling tool having a handling portion and a mounting portion extending at an extremity of said handling portion, said blade being mounted to said mounting portion, said blade being substantially planar and comprising a first surface and a second surface, and a substantially curved cutting edge, wherein at least one of said first and second surfaces comprises markings substantially parallel to said cutting edge such that said markings provide a substantially constant indication of a depth of said cutting edge with respect to a tissue when an orientation of said blade with respect to said tissue is changed.

15. A combination as claimed in claim 14, wherein said markings are substantially parallel lines.

16. A combination as claimed in claim 15, wherein said lines are formed on said at least one of said first and second surfaces of said blade.

17. A combination as claimed in claim 15, wherein said lines are equidistant.

18. A combination as claimed in claim 14, wherein said markings are substantially parallel and visually different areas.

19. A combination as claimed in claim 18, wherein said areas are textured.

20. A combination as claimed in claim 14, wherein both said first surface and said second surface comprise markings substantially parallel to said cutting edge.

21. A surgical blade, said blade being substantially planar and comprising two sides and a cutting edge, at least one of said sides comprising at least one marking substantially following said cutting edge, said at least one marking being configured to provide a substantially constant indication of a selected depth of said cutting edge with respect to a tissue when an orientation of said blade with respect to said tissue is changed.

22. A blade as claimed in claim 21, wherein said at least one marking is at least one line substantially parallel to said cutting edge.

23. A blade as claimed in claim 22, wherein said at least one area is textured.

24. A blade as claimed in claim 21, wherein said at least one marking is at least one visually distinct area substantially parallel to said cutting edge.

25. A surgical blade, said blade being substantially planar and comprising a first surface, a second surface, and a substantially curved cutting edge, wherein at least one of said first and second surfaces comprises at least one marking substantially parallel to said cutting edge, said at least one marking being configured to provide a substantially constant indication of a depth of said cutting edge with respect to a tissue when an orientation of said blade with respect to said tissue is changed.

26. A blade as claimed in claim 25, wherein said at least one marking is at least one line.

27. A blade as claimed in claim 25, wherein said at least one marking is at least one visually distinct area.

28. A blade as claimed in claim 27, wherein said at least one area is textured.

29. A blade as claimed in claim 25, wherein both said first surface and said second surface comprise at least one marking substantially parallel to said cutting edge.

30. A surgical blade in combination with a handling tool, said handling tool having a handling portion and a mounting portion extending at an extremity of said handling portion, said blade being mounted to said mounting portion, said blade being substantially planar and comprising a first surface, a second surface, and a substantially curved cutting edge, wherein at least one of said first and second surfaces comprises at least one marking substantially parallel to said cutting edge such that said at least one marking provides a substantially constant indication of a depth of said cutting edge with respect to a tissue when an orientation of said blade with respect to said tissue is changed.

31. A combination as claimed in claim 30, wherein said at least one marking is at least one line.

32. A combination as claimed in claim 30, wherein said at least one marking is at least one visually distinct area.

33. A combination as claimed in claim 32, wherein said at least one area is textured.

34. A combination as claimed in claim 30, wherein both said first surface and said second surface comprise at least one marking substantially parallel to said cutting edge.

* * * * *